United States Patent [19]

Ito

[11] 4,162,761
[45] Jul. 31, 1979

[54] FLOW-THROUGH COIL PLANET CENTRIFUGES WITH ADJUSTABLE ROTATION/REVOLUTION OF COLUMN

[75] Inventor: Yoichiro Ito, Bethesda, Md.

[73] Assignee: The United States of America as represented by the Department of Health, Education and Welfare, Washington, D.C.

[21] Appl. No.: 856,172

[22] Filed: Nov. 30, 1977

[51] Int. Cl.² .......................... B04B 5/02; B04B 9/08
[52] U.S. Cl. ...................................... 233/24; 233/25; 210/198 C
[58] Field of Search ...................... 233/23 R, 23 A, 24, 233/25, 26, 1 A, 17; 74/797; 210/31 C, 198 C

[56] References Cited

U.S. PATENT DOCUMENTS

| | | | |
|---|---|---|---|
| 3,420,436 | 1/1969 | Ito | 233/17 |
| 3,775,309 | 11/1973 | Ito et al. | 210/198 C |
| 3,882,716 | 5/1975 | Beiman | 233/25 |
| 4,058,460 | 11/1977 | Ito | 210/198 C |

Primary Examiner—George H. Krizmanich
Attorney, Agent, or Firm—Browdy and Neimark

[57] ABSTRACT

A flow-through coil planet centrifuge has variable rotation-revolution (r/R) speed ratios. The rotation and revolution are continuously adjustable by using separate variable-speed drive motors. A first embodiment employs rotating seals, whereas a second embodiment is without rotating seals. In the rotating seal embodiment the flow tubes are rotated synchronously with the column to avoid twisting; in the non-rotating seal embodiment a system of gearing and belts compensates for the rotation and revolution of the column relative to a stationary tube support to avoid twisting of the flow tubes.

10 Claims, 5 Drawing Figures

FLOW-THROUGH COIL PLANET CENTRIFUGES WITH ADJUSTABLE ROTATION/REVOLUTION OF COLUMN

FIELD OF THE INVENTION

This invention relates to centrifugal liquid processing apparatus, and more particularly to a coil planet centrifuge apparatus of the flow-through type having a variable rotation/revolution ratio.

BACKGROUND OF THE INVENTION

Coil planet centrifuge devices for particle separation were first developed employing end-closed coiled tubes. This type of centrifuge device is described in U.S. Pat. No. 3,420,436 to Y. Ito. This original type of centrifuge apparatus was designed to obtain predetermined specific rotation/revolution (r/R) ratios of the column holder, such as 1/100, 1/200, 1/300 and 1/500. The capability of the system has been demonstrated by the separation of particles using both single phase and two-phase solvent systems.

However, the above-mentioned prior system lacks continuous flow-through capability, resulting in limited efficiency and in difficulty in the continuous monitoring and fractionization of the separated samples.

Recently, various types of flow-through centrifuge devices have been developed to carry out countercurrent chromatography (U.S. Pat. Nos. 3,775,309; 3,856,669; 3,994,805; and 4,058,460) and cell separations (U.S. Ser. No. 661,114) without the use of rotating seals. However, all these systems have fixed r/R values, of either 1 or zero, and thus lack versatility in separation (also see U.S. Pat. No. 3,986,442).

SUMMARY OF THE INVENTION

Accordingly, a main object of the invention is to overcome the deficiencies and disadvantages, such as mentioned above and/or inherent in the above-mentioned prior art devices.

Another object is to provide for improved and more versatile separation and/or fractionation of components in a mixture.

A further object of the invention is to provide an improved coil planet centrifuge device which has continuous flow-through capability, which is highly efficient, and which facilitates the continuous monitoring and fractionation of separated samples.

A still further object of the invention is to provide an improved coil planet centrifuge apparatus of the flow-through type which provides continuous adjustability of the rotation/revolution (r/R) ratio of its column holder and which therefore is continuously adjustable to meet a wide range of separation requirements, thus providing the apparatus with a high degree of versatility in separation.

A still further object of the invention is to provide an improved coil planet centrifuge apparatus of the flow-through type which includes separate continuously variable-speed motors respectively for rotating the shaft of its column holder and for simultaneously revolving the column holder around the central axis of the apparatus, whereby to provide continuous adjustability of the rotation/revolution ratio (r/R) of the column holder and to enable the apparatus to cover a wide range of separation requirements with high efficiency and versatility.

A still further object of the invention is to provide an improved coil planet centrifuge apparatus of the flow-through type with continuous adjustability of the rotation/revolution ratio (r/R) of its column holder over a wide range of separation requirements and having means to avoid twisting of its flow tubes without requiring the use of rotating seals.

The present invention is useful in the separation of biological materials from cells, viruses, macromolecules to small molecular weight compounds, and at a very high purity.

BRIEF DESCRIPTION OF THE DRAWINGS

Further objects and advantages of the invention and a better understanding thereof will become apparent from the following description of specific exemplary embodiments and from the accompanying drawing thereof, wherein.

DESCRIPTION OF PREFERRED EMBODIMENTS

Figure 1:
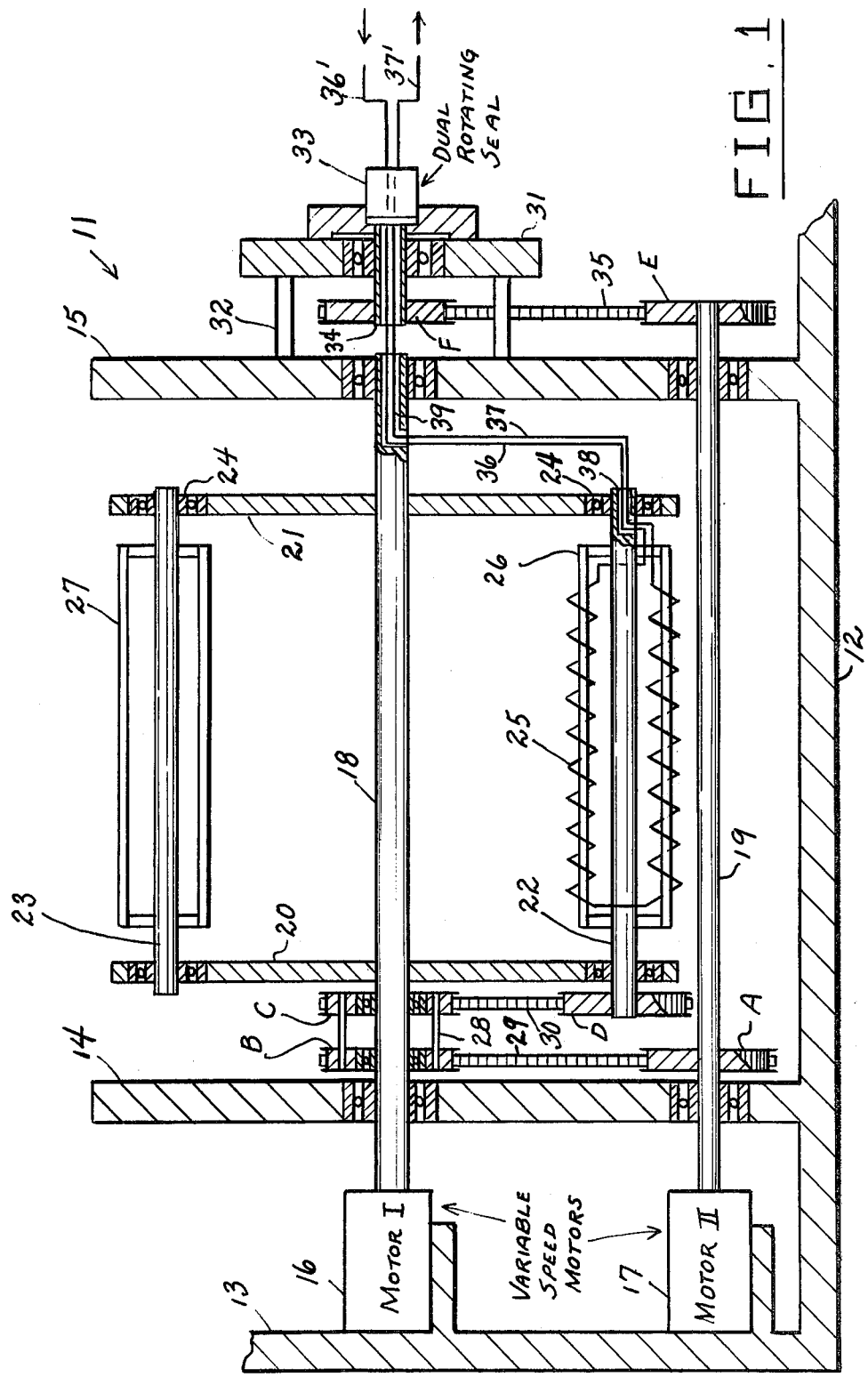
FIG. 1 is vertical cross-sectional view of a flow-through coil planet centrifuge apparatus constructed according to the present invention, of a type employing rotating seals.

Referring to the drawing, and more particularly to FIG. 1, a first embodiment 11 is shown of a coil planet centrifuge apparatus according to the present invention. The apparatus 11 comprises a stationary support 12 having spaced upstanding arms 13, 14 and 15. A first motor 16 is rigidly secured on the arm 13 and a second motor 17 is likewise rigidly secured on arm 13, spaced below the motor 16, as viewed in FIG. 1. The motor 16 has a shaft 18 suitably journalled in arms 14, 15, and the motor 17 has a shaft 19 likewise journalled in these arms 14, 15.

Secured rigidly on the shaft 18 are the spaced parallel rotary wings 20, 21. Journalled respectively in the end portions of rhe rotary wings 20, 21 by means of suitable bearings 24 are a column holder shaft 22 and a counterweight shaft 23. A coiled capillary column 25 is supported on a column holder 26 secured on the shaft 22. A counterweight member 27 is secured on the shaft 23 for providing proper balancing of the apparatus.

Secured rigidly on one end of shaft 22 is a toothed pulley, or sprocket wheel, D. Secured rigidly on the shaft 19 of motor 17 is another toothed pulley A, which may be identical to the pulley D. Journalled to rotate relative to the shaft 18 and aligned respectively with pulleys A and D are idler toothed pulleys B and C, which again may be identical to pulleys A and D, and which are rigidly connected together, as by coupling pins 28. Drive pulley A is drivingly coupled to pulley B by a toothed belt 29 or the like and pulley C is drivingly coupled to pulley D by a similarly toothed belt 30. Thus, motor 17 is drivingly connected to the column holder shaft 22.

The motor shaft 19 has an additional toothed pulley E, which may be identical to the pulleys A through D, rigidly secured on its end portion. A bracket plate 31 is rigidly secured in outwardly spaced relation to the arm 15, as by connection rods 32. A conventional dual rotating seal unit has a stationary portion 33 mounted on the bracket 31 in alignment with the shaft 18 and has a rotating sleeve-like portion 34 which is journalled in the bracket 31 and on which is rigidly secured a toothed pulley F, aligned with and preferably identical to toothed pulley E.

Stationary inlet and outlet external tube portions 36′ and 37′ are connected to the stationary rotary seal ports of the stationary portion 33 of the dual rotating seal unit. The toothed pulleys E and F are drivingly coupled by a toothed belt 35. Thus, motor 17 also drives the rotating portion 34 of the rotating seal through the pulleys E, F and the belt 35, these pulleys E, F preferably being both identical to pulley A. Therefore, the rotatable portion 34 of the rotating seal assembly rotates synchronously with column holder 26. The flow tubes, shown at 36, 37, are led through a passage 38 formed in the end of column holder shaft 22 and which serves as a guide means for the flow tubes, and then extend loosely through an end passage 39 of motor shaft 18, thence being connected in a conventional manner to the appropriate ports of the rotating portion 34 of dual rotating seal assembly, the end passage 39 and the rotating portion 34 serving as a tube exit guide means.

This arrangement allows the column holder 26 to rotate about its own axis and simultaneously revolve around the axis of the central shaft 18 of the centrifuge apparatus at variable rates, according to the adjusted speeds of the motors 16, 17.

When the shaft 18 of the first motor 16 rotates at a selected speed $\omega$ while the second motor 17 is at rest, the column holder 26 revolves with the rotary wings 20, 21 around the central axis of shaft 18 at said speed $\omega$. This motion also causes counter-rotation of the column holder 26 about its own axis at the same angular velocity, due to the coupling of pulley D to pulley C (which is stationary since the second motor 17 is at rest). Although the rotatable portion 34 of the dual rotating seal unit is not moving, the flow tubes 36, 37 do not twist because the counter-rotaton of the column holder 26 cancels out the revolutional effect.

When the shaft 19 of the second motor 17 rotates at a speed $\omega$ while the first motor 16 is at rest, the column holder 26 rotates around its own axis at said speed $\omega$ on the stationary wings 20, 21 by means of pulleys A, B, C and D coupled by the drive belts 29, 30. Motor 17 also drives the rotatable portion 34 of the dual rotating seal unit 33 at said speed $\omega$ to prevent twisting of the flow tubes 36, 37.

When the shafts of both motors 16 and 17 are rotating at the same angular velocity $\omega$, the column holder 26 revolves around the central axis of the apparatus at a speed $\omega$ while rotation of the column holder 26 is not produced, because the second motor 17 drives pulley C and D at the same rate about the central axis of the apparatus and about the axis of shaft 22, respectively.

In general, when motors 16 and 17 are driven at the rates of $\omega_I$ and $\omega_{II}$ respectively, the column holder 26 revolves around the central axis of the apparatus at a speed $\omega_I$ while it also revolves around its own axis at a speed $\omega_{II}-\omega_I$ without twisting the flow tubes 36, 37. Thus, since the rotation/revolution ratio (r/R) of the column holder is equal to $(\omega_{II}-\omega_I/\omega_I)$, this ratio can be conveniently adjusted to any desired value by choosing the speeds of the motors 16 and 17.

The above specific conditions hold true in the simplest design, wherein pulleys A through F are identical. However, the relative number of teeth of these pulleys may be modified without departing from the basic principles employed in the above-described centrifuge apparatus. In order to prevent twisting of the flow tubes 36, 37 it is necessary to satisfy the following equation:

$$(T_A/T_B)\cdot(T_C/T_D)=T_E/T_F \tag{1}$$

where $T_A$ through $T_F$ denote the tooth numbers of the respective pulleys A through F.

Figure 2:
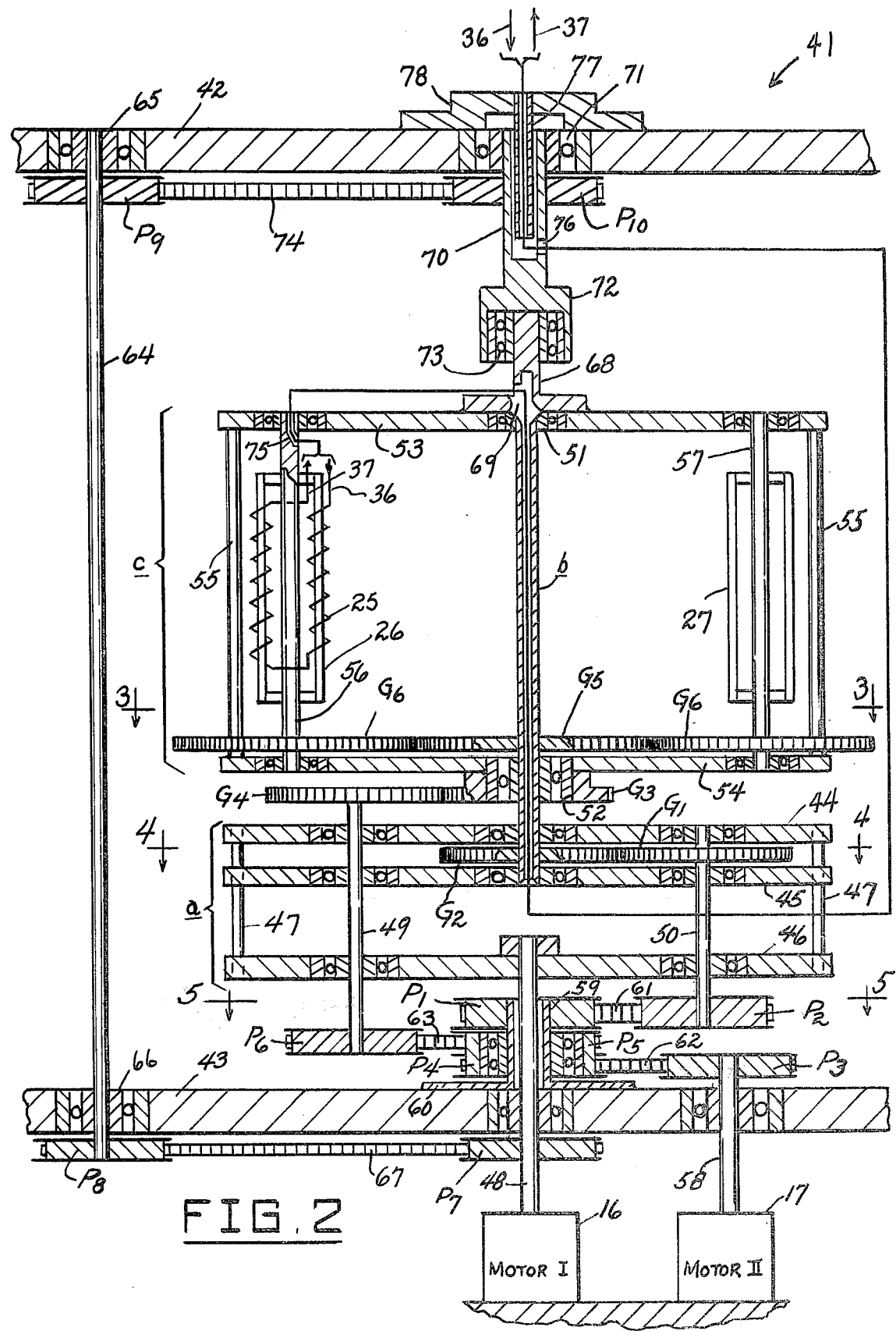
FIG. 2 is a vertical cross-sectional view of another form of flow-through coil planet centrifuge apparatus according to the present invention, of a type not employing rotating seals.
Figure 3:
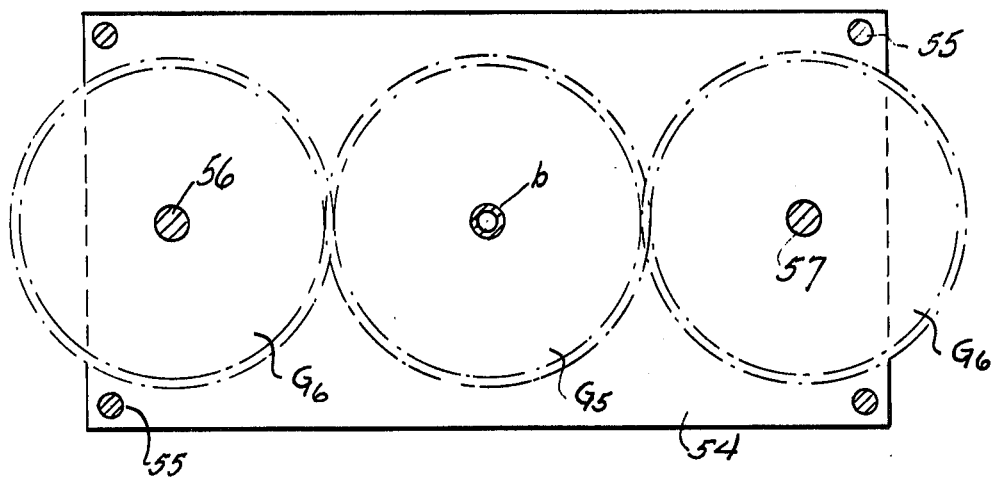
FIG. 3 is a cross-sectional view taken substantially on the line 3—3 of FIG. 2.
Figure 4:
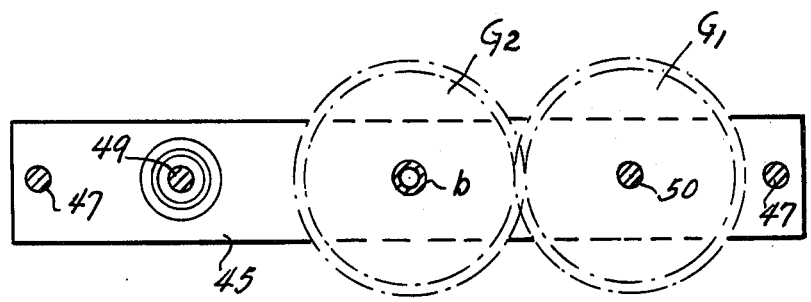
FIG. 4 is a cross-sectional view taken substantially on the line 4—4 of FIG. 2.
Figure 5:
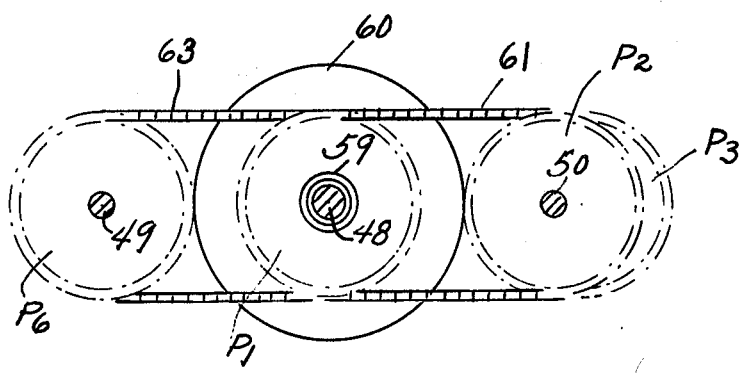
FIG. 5 is a cross-sectional view taken substantially on the line 5—5 of FIG. 2.

FIGS. 2 to 5 illustrate another form of coil planet centrifuge apparatus 41 according to the present invention, of a type not employing rotating seals. Such apparatus 41 is supported between spaced stationary wall members 42 and 43 and generally comprises a rotor assembly having three major parts, namely, parts a, b and c, as illustrated in FIG. 2.

Part a consists of three spaced parallel plates 44, 45 and 46 rigidly connected together, as by a plurality of dowel rods 47. A first motor 16, suitably mounted on a stationary support, has a shaft 48 which is journalled in lower wall member 43, as viewed in FIG. 2, and is rigidly secured to the center portion of plate 46 to define an axial driving shaft for part a. The part a rotatably supports three vertical rotary elements, as viewed in FIG. 2, namely, (1) a hollow upstanding central shaft, comprising part b, axially aligned with motor shaft 48 and rotatably mounted in the spaced upper plate members 44 and 45, (2) a left vertical countershaft 49 journalled in plates 44, 45 and 46 and projecting upwardly and downwardly therefrom, and (3) a right vertical countershaft 50 journalled in said plates 44, 45 and 46 and projecting downwardly therefrom. Said three rotary elements are provided with conventional bearings including thrust bearing means, not shown, to hold the rotary elements against axial displacement.

Part b, comprising a hollow vertical shaft, as viewed in FIG. 2, which is rotatably mounted centrally in part a, as above described, in turn supports part c by means of upper and lower bearing assemblies 51 and 52. Secured on hollow shaft b are spaced gears $G_2$ and $G_5$. The lower gear, $G_2$, meshingly engages with a gear $G_1$ mounted on the countershaft 50 of part a, and the upper gear $G_5$ meshingly engages with opposite gears $G_6$, $G_6$ which are included in part c.

Part c comprises a pair of spaced parallel wings 53 and 54 rigidly connected together, as by a plurality of vertical dowel rods 55, the members 53 and 54 being journalled to rotate around hollow shaft b as a central axis. The lower rotary wing 54 has a gear $G_3$ which meshingly engages with a gear $G_4$ secured on the top end of countershaft 49 of part a. Journalled respectively between the opposite end portions of rotary wings 53 and 54 are vertical rotary shafts 56 and 57, each provided with an above-mentioned gear $G_6$ in meshing engagement with gear $G_5$. Mounted on shaft 56 is a column holder 26 carrying a coiled capillary tube column 25 having inlet and outlet tubes 36 and 37. Mounted on shaft 57 is the counterweight member 27.

A second motor 17, mounted on the stationary support adjacent motor 16, has a shaft 58 extending parallel to shaft 48 and being suitably journalled in wall member 43. Concentric with shaft 48 is an upstanding sleeve member 59 having an annular base flange 60 which is rigidly secured to wall member 43. Rigidly secured on the top end portion of sleeve member 59 is a stationary toothed pulley $P_1$. Secured on the depending portion of countershaft 50 is a toothed pulley $P_2$ which is drivingly coupled to stationary toothed pulley $P_1$ by a toothed belt 61.

Journalled on sleeve member 59 below toothed pulley $P_1$ is a double toothed pulley having an upper toothed pulley element $P_5$ and a lower toothed pulley element $P_4$ integrally united. Secured on the top end portion of motor shaft 58 is a toothed pulley $P_3$ drivingly coupled to pulley element $P_4$ by a toothed belt 62. Secured on the bottom end portion of countershaft 49 is a toothed pulley $P_6$ which is drivingly coupled to toothed pulley element $P_5$ by a toothed belt 63.

Designated at 64 is a third countershaft which is journalled in wall members 42 and 43, as by suitable supporting bearing assemblies 65, 66, and which projects below wall member 43, as viewed in FIG. 2. A toothed pulley $P_8$ is secured on the lower end of countershaft 64 and is drivingly coupled to a toothed pulley $P_7$ on motor shaft 48 by a toothed belt 67.

A flanged hollow stud member 68 is centrally rigidly secured on rotary wing member 53 in axial alignment with hollow shaft b and has a side-opening tubing passage 69 in communication with said hollow shaft b. A coupling sleeve membger 70 is supportingly journalled in wall member 42 by a suitable bearing assembly 71, in axial alignment with stud member 68 and has an enlarged hollow bottom boss 72 which receives said stud member 68 and rotatably supports same by means of a suitable bearing assembly 73.

A toothed pulley $P_9$ is secured on countershaft 64 adjacent bearing assembly 65 and is drivingly coupled to a toothed pulley $P_{10}$ on sleeve member 70 by a toothed belt 74.

The flow tubes 36,37 of the column 25 are first led through a side-opening passage 75 in the top end of rotary shaft 56, as viewed in FIG. 2, then pass through the side-opening passage 69 of stud member 68, then pass loosely through the hollow shaft b, then pass through the space between the plate members 45 and 46, then pass upwardly and through a side opening 76 into sleeve 70, and then extend tightly and supportingly through a stationary pipe 77, emerging above the top end of said pipe. Pipe 77 is rigidly secured to a stationary supporting bracket 78 which is rigidly secured in turn to wall member 42. The portions of the flow tubes 36, 37 between aperture 76 and the bottom end of hollow shaft b are supported by any suitable means so that they will always remain clear of part c of the assembly. This can be accomplished, for example, by employing thin, long tube supporters extending from the middle plate 45 of part a and from the sleeve member 70 subjacent side hole 76.

The first and second motors 16 and 17 are employed to drive the rotor assembly. When motor 16 drives parts a at a speed $\omega_I$, the stationary pulley $P_1$ generates counter-rotation of pulley $P_2$ through the toothed belt 61, and the countershaft 50 rotates at a speed $-\omega_I$ with respect to the rotating part a. This motion is further conveyed to part b by the gearing $G_1,G_2$, which have a 1:1 gear ratio. Thus, part b rotates at a speed $2\omega_I$, or at a speed $\omega_I$ with respect to the rotating part a. The motion of part c, however, also depends on the motion of shaft 58 of the second motor 17.

If motor 17 is at rest, pulley element $P_5$ is stationary, as is pulley $P_1$, and the second countershaft 49 counterrotates (by the action of belt 63 and pulley $P_6$) at the speed $\omega_I$ (produced by motor 16), as does the first countershaft 50 (pulleys $P_1,P_2P_5$ and $P_6$ are identical). This motion is similarly conveyed to the rotary wings 53,54 of part c by the gearing $G_4,G_3$, which have a 1:1 gear ratio, resulting in the rotation of the rotary wings 53,54 of part c at a speed $2\omega_I$, the same angular velocity as that of part b. Under this condition the gearing engagement of gear $G_5$ with gears $G_6$ produces no motion of the rotary shafts 56,57 of part c with respect to the rotary wings 53,54. Said shafts 56.57 (shaft 56 is the column holder shaft) merely revolve with part b at a speed of $2\omega_I$.

When the shaft 58 of second motor 17 rotates at a speed $\omega_{II}$, pulley $P_5$ rotates at $\omega_{II}$ because of the coupling between pulleys $P_3$ and $P_4$, whereby the coupling between pulleys $P_5$ and $P_6$ causes the rate of counter-rotation of the second countershaft 49 to be modified to a speed $(\omega_I-\omega_{II})$. This motion further modifies the motion of the rotary wings 53,54 of part c by the 1:1 gearing between gears $G_4$ and $G_3$. Thus, the rotary wings 53,54 rotate at an absolute speed of $(2\omega_I-\omega_{II})$, or at a speed $(\omega_I-\omega_{II})$ with respect to the rotating part a. The gearing engagement of gears $G_5$, $G_6$, which have a 1:1 gear ratio, then allows the rotary shafts 56,57 to counter-rotate around their own axes at a speed $\omega_{II}$, while revolving around the central axis of the apparatus at a speed $(2\omega_I-\omega_{II})$. This gives $$r/R=-\omega_{II}/((2\omega_I-\omega_{II})) \qquad (2)$$

and, therefore, any combination of revolutional and rotational speeds of the column holder 26 can be obtained by selecting the proper values for $\omega_I$ and $\omega_{II}$.

Toothed pulley $P_{10}$ on coupling sleeve member 70 is rotated at a speed $\omega_I$ by means of pulley $P_7$ on motor shaft 48, belt 67, pulley $P_8$, shaft 64, pulley $P_9$ and belt 74. Pulleys $P_7$, $P_8$, $P_9$ and $P_{10}$ are identical.

Under the above-described conditions, the flow tubes 36,37 do not twist, regardless of the motions of the shafts 48,58 of the two motors 16,17.

The portions of the flow tubes between the top of the column holder rotary shaft 56 and the central hollow shaft b do not twist because the 1:1 ratio gear coupling between gears $G_5$ and $G_6$ compels the column holder rotary shaft 56 and the central hollow shaft b to rotate always at the same speed but in the opposite directions with respect to the rotating rotary wings 53,54 of part c. The portions of the flow tubes 36,37 hung between the lower end of the central hollow shaft b and the top stationary support tube 77 do not twist because the revolutional twisting effect of the rotation of part a on the flow tubes is compensated for by the rotational effect of the column holder 26 relative to the wing members 53,54. Thus, the system shown in FIG. 2 allows any desired rotational and revolutional speeds of the column holder shaft 56 without twisting the flow tubes.

A typical design according to FIG. 2 may employ identical pulleys $P_1$ to $P_{10}$ and respective sets of identical meshing gears, namely, identical gears $G_1,G_2$, identical gears $G_3,G_4$ and identical gears $G_5,G_6,G_6$. This may be modified without affecting the functional operation of the system. In order to maintain the flow tubes always untwisted it is necessary to satisfy the following equations:

$$T_{P_1}/T_{P_2}=T_{G_2}/T_{G_1} \qquad (3)$$

$$T_{P7}/T_{P8} = T_{P10}/T_{P9} \tag{4}$$

$$T_{G6} = T_{G5} \tag{5}$$

where T denotes the tooth number for the subscript-indicated pulley or gear.

The tooth number of pulleys $P_3$, $P_4$, $P_5$ and $P_6$, and of gears $G_3$ and $G_4$ may be modified to any practical values to change the motion of the column holder rotary shaft 56 in Equation (2) to $$r/R = -k\omega_{II}/(2\omega_I - k\omega_{II}) \tag{6}$$

where $$k = T_{P3}/T_{P4} \cdot T_{P5}/T_{P6} \cdot T_{G4}/T_{G3} \tag{7}$$

The two systems above described provide substantially identical performance in that both provide adjustable r/R at a given R or r value of the column holder rotary shaft, with a continuous flow-through capacity. The first-described system (FIG. 1) is simple but has the minor disadvantage of employing a dual rotating seal. The second-described system (FIG. 2) has a more complex design, but it allows use of a high column pressure without leakage, with accurate control of r/R values over a wide range.

The following are typical applications of the above-described apparatus:

1. Particle separation with a single phase solvent system.

The helical column is first filled with a solvent and a sample solution containing dispersed particles is introduced into the column, followed by elution with the solvent while the column is spun at desired rates or r and R. Due to the screwing action produced by rotation of the helical column under a centrifugal force field, denser and/or greater diameter particles tend to stay or delay in the column while lighter and/or smaller diameter particles are eluted quickly through the column and fractionated. In order to separate live cells with a physiological solution, it is necessary to apply rather small r/R of 1/50 to 1/1000. These operational conditions are not available in the previously used apparatus except for original coil planet centrifuge types which lack the flow-through capability.

2. Separation of particles and macromolecules in polymer two-phase solvent systems.

The column is first filled with the stationary phase (either upper or lower phase) of an equilibrated polymer phase system. Then a sample solution is introduced into the column, followed by elution with the mobile phase while the column is spun at desired rates of r and R. Particles or solutes which have higher partition coefficients are quickly eluted through the column while those with lower partition coefficients are retained in the column, resulting in a chromatographic separation of the samples.

While certain specific embodiments of improved flow-through coil planet centrifuge apparatus have been disclosed in the foregoing description, it will be understood that various modifications within the scope of the invention may occur to those skilled in the art. Therefore it is intended that adaptations and modifications should and are not intended to be comprehended within the meaning and range of equivalents of the disclosed embodiments. For example, it will be readily evident that toothed pulleys and toothed belts may be replaced by functionally similar means, e.g. drive chains, drive belts, etc.

What is claimed is:

1. A flow-through coil planet centrifuge having a central rotational axis, comprising, two independent stationary motors one of which is mounted out of the central rotational axis, centrifuge rotor means rotatably mounted on the central rotational axis, means drivingly coupling one of said motors to said rotor means, a coiled tubular column and including an inlet and an outlet end both extending outside the rotor means along the central rotational axis, means rotatably mounting said column on said rotor means for rotation on an axis parallel to and spaced from the central rotational axis, means to feed fluid into the inlet end of said tubular column and out the outlet end during operation of the centrifuge, and planetary means drivingly coupling the other motor to said coiled column.

2. The coil planet centrifuge of claim 1, and wherein at least one of said motors is of the continuously variable-speed type.

3. The coil planet centrifuge of claim 1, and wherein both of said motors are of the continuously variable-speed type.

4. The coil planet centrifuge of claim 1, and wherein said column is provided with inlet and outlet flow-through tubes extending respectively to said inlet and outlet ends and with guide means to support said tubes along the axis of rotation of the column, exit guide means receiving said tubes, means rotatably mounting said exit guide means coaxially with said rotor means, means drivingly coupling said tube exit guide means to said one motor, and means for rotating said tube exit guide means synchronously with said column.

5. In a flow-through-coil planet centrifuge, two independent stationary motors, rotatably-mounted centrifuge rotor means, means drivingly coupling one of said motors to said rotor means, a coiled tubular column, means rotatably mounting said column on said rotor means for rotation on an axis parallel to and spaced from the rotational axis of said rotor means, planetary means drivingly coupling the other motor to said coiled column, inlet and outlet flow-through tubes, guide means to support said tubes along the axis of rotation of said column, exit guide means receiving said tubes, means rotatably mounting said exit guide means coaxially with said rotor means, means drivingly coupling said tube exit guide means to one of said motors, and means to rotate said column at a speed sufficient to avoid twisting of the inlet and outlet tubes between said first-named guide means and said tube exit guide means.

6. The coil planet centrifuge of claim 5, and wherein a dual rotating seal is provided in axial alignment with said rotor means, said rotating seal having an outer stationary portion and an inner rotating portion, said tube exit guide means forming a part of the rotating seal inner rotating portion.

7. The coil planet centrifuge of claim 5, and wherein said other motor is provided with power transmission means coupling it to said rotor means including a first pair of coupled toothed pulleys A and B having tooth numbers $T_A$, $T_B$ and a second pair of coupled toothed pulleys C and D having tooth numbers $T_C$ and $T_D$, the pulleys B and C being rigidly coaxially connected together, and with power transmission means coupling said other motor to said tube exit guide means including a third pair of coupled toothed pulley E and F having tooth numbers $T_E$ and $T_F$, the respective tooth numbers being in accordance with $$T_A/T_B \cdot T_C/T_D = T_E/T_F$$

8. The coil planet centrifuge of claim 5, and wherein transmission means is provided between said one motor and said tube exit guide means including a first pair of coupled toothed pulleys $P_7$, $P_8$ having tooth numbers $T_{P7}$, $T_{P8}$ and a second pair of coupled toothed pulleys $P_9$, $P_{10}$ having tooth numbers $T_{P9}$, $T_{P10}$, the pulleys $P_8$ and $P_9$ being rigidly coaxially connected together, the respective tooth numbers being in accordance with $$T_{P7}/T_{P8} = T_{P10}/T_{P9},$$

wherein transmission means is provided between said one motor and said rotor means including a third pair of coupled toothed pulleys $P_1$, $P_2$ having tooth numbers $T_{P1}$, $T_{P2}$, and a first pair of meshing gears $G_1$, $G_2$ having tooth numbers $T_{G1}$, $T_{G2}$, and wherein transmission means is provided between said one motor and said column including meshing gears $G_5$, $G_6$ having tooth numbers $T_{G5}$, $T_{G6}$, the respective tooth numbers being in accordance with $$T_{P1}/T_{P2} = T_{G2}/T_{G1} \text{ and } T_{G6} = T_{G5}.$$

9. In a flow-through coil planet centrifuge, two independent stationary motors, rotatably-mounted centrifuge rotor means, means drivingly coupling one of said motors to said rotor means, a coiled tubular column having inlet and outlet flow-through tubes and with guide means to support said tubes along the axis of rotation of the column, exit guide means receiving said tubes, means rotatably mounting said column on said rotor means for rotation on an axis parallel to and spaced from the rotational axis of said rotor means, means rotatably mounting said exit guide means coaxially with said rotor means, means drivingly coupling said tube exit guide means to one of said motors, means for rotating said tube exit guide means synchronously with said column, and planetary means drivingly coupling the other motor to said coiled column.

10. In a flow-through coil planet centrifuge, two independent stationary motors, rotatably-mounted centrifuge rotor means, means drivingly coupling one of said motors to said rotor means, a coiled tubular member, means rotatably mounting said column on said rotor means for rotation on an axis parallel to and spaced from the rotational axis of said rotor means, planetary means drivingly coupling the other motor to said coiled column, inlet and outlet flow-through tubes and guide means to support said tubes along the axis of rotation of the coiled tubular column, exit guide means receiving said tubes, means rotatably mounting said exit guide means coaxially with said rotor means, means drivingly coupling said tube exit guide means to said other motor, and means for rotating said column synchronously with said tube exit guide means.

* * * * *